(12) United States Patent
Moreau et al.

(10) Patent No.: US 10,779,869 B2
(45) Date of Patent: Sep. 22, 2020

(54) IMPLANT DEVICE

(71) Applicant: NEURO FRANCE IMPLANTS, La Ville-aux-Clercs (FR)

(72) Inventors: Patrice Moreau, Boursay (FR); Karin Worner, Epuisay (FR); Gilles Missenard, Paris (FR); Patrick Tropiano, Marseilles (FR); Charles Court, Versailles (FR)

(73) Assignee: NEURO FRANCE IMPLANTS, La Ville-aux-Clercs (FR)

( * ) Notice: Subject to any disclaimer, the term of this patent is extended or adjusted under 35 U.S.C. 154(b) by 79 days.

(21) Appl. No.: 16/069,948

(22) PCT Filed: Jan. 13, 2017

(86) PCT No.: PCT/FR2017/050074
§ 371 (c)(1),
(2) Date: Jul. 13, 2018

(87) PCT Pub. No.: WO2017/121968
PCT Pub. Date: Jul. 20, 2017

(65) Prior Publication Data
US 2019/0015143 A1    Jan. 17, 2019

(30) Foreign Application Priority Data
Jan. 13, 2016   (FR) .................................... 16 50268

(51) Int. Cl.
*A61B 17/86* (2006.01)
*A61B 17/70* (2006.01)

(52) U.S. Cl.
CPC ........ *A61B 17/863* (2013.01); *A61B 17/7002* (2013.01); *A61B 17/7032* (2013.01);
(Continued)

(58) Field of Classification Search
CPC ... A61B 17/86; A61B 17/863; A61B 17/8635; A61B 17/864
See application file for complete search history.

(56) References Cited

U.S. PATENT DOCUMENTS 3,271,075 A    9/1966  Good
4,041,939 A *  8/1977  Hall .................... A61B 17/7022
                                            606/254

(Continued)

FOREIGN PATENT DOCUMENTS

DE   10 2013 001933 A1   3/2014
FR         2880254 A1    7/2006
WO      2010148299 A1   12/2010

*Primary Examiner* — Anu Ramana
(74) *Attorney, Agent, or Firm* — Craft Chu PLLC; Andrew W. Chu

(57) ABSTRACT

An implant device is used for maintaining a distraction or compression element and includes a rod linked to implants by support devices having a threaded stud and a head for interaction with a support piece. The support piece has a device for attaching and blocking a distraction or compression element. The threaded piece includes two zones, namely a distal end zone having a conical profile and a screw thread with wide turns, configured for cancellous bone, and a proximal zone having a conical profile with a conicity angle smaller than the conicity angle of the distal portion, with a narrow screw thread, configured for bone cortex, namely including sharp, thin, deep screw threads, whereas the web is flat.

8 Claims, 1 Drawing Sheet

(52) U.S. Cl.
CPC ........ *A61B 17/7037* (2013.01); *A61B 17/864* (2013.01); *A61B 17/8605* (2013.01); *A61B 17/8625* (2013.01); *A61B 17/8635* (2013.01)

(56) References Cited

U.S. PATENT DOCUMENTS

| | | | | |
|---|---|---|---|---|
| 5,120,171 | A | * | 6/1992 | Lasner ................. A61B 17/863 411/308 |
| 6,030,162 | A | * | 2/2000 | Huebner ............ A61B 17/1682 411/263 |
| 6,039,149 | A | | 3/2000 | Bedja et al. |
| 7,207,992 | B2 | * | 4/2007 | Ritland .............. A61B 17/7007 606/86 A |
| 7,220,262 | B1 | * | 5/2007 | Hynes ................ A61B 17/7011 606/279 |
| 7,611,518 | B2 | * | 11/2009 | Walder ................ A61B 17/704 606/246 |
| 8,128,671 | B2 | * | 3/2012 | Taylor ................. A61B 17/863 411/308 |
| D710,031 | S | | 7/2014 | Simpson et al. |
| 9,179,955 | B2 | * | 11/2015 | Whipple ............. A61B 17/863 |
| 2003/0074002 | A1 | | 4/2003 | West |
| 2006/0084993 | A1 | * | 4/2006 | Landry ............. A61B 17/1604 606/86 A |
| 2013/0253594 | A1 | | 9/2013 | Zucherman |
| 2014/0012334 | A1 | | 1/2014 | Armstrong |
| 2014/0121703 | A1 | | 5/2014 | Jackson |
| 2015/0196336 | A1 | | 7/2015 | Whipple |

* cited by examiner

IMPLANT DEVICE

CROSS-REFERENCE TO RELATED APPLICATIONS

See Application Data Sheet.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

The present invention relates to an implant device for osteosynthesis, and in particular for vertebral osteosynthesis.

More particularly, the present invention relates to an implant for maintaining a distraction or compression element generally consisting of a bar connected to implants through support means, or a plate pierced with holes for the passage of implants.

2. Description of Related Art Including Information Disclosed Under 37 CFR 1.97 and 37 CFR 1.98

Such an implant is for example described in document FR 2,880,254. It is of the type consisting of a screw comprising a threaded shank, as well as a head provided with a cavity for maneuvering thereof, and which has a spherical or partially spherical part intended to cooperate with a support piece able to pivot on said head and to be immobilized therein, said support piece including means for fastening and blocking a distraction or compression element.

Many alternatives of these implant devices exist, which essentially differ in terms of the means for fastening and blocking a distraction or compression bar.

However, all of the implant devices have the same drawbacks, namely essentially anchoring that may be unreliable, as well as fairly rapid bone scarring.

Some have proposed threaded implants that have distinct zones in the longitudinal direction, in particular while having different pitches, like in documents US 2013253594 and US 2014012334, with the drawback that the part that includes a longer pitch accelerates the movement speed of the implant, such that the pitch of the part that includes a shorter pitch tends to drill a hole rather than performing a tapping, which is detrimental to the anchoring.

One of the main problems encountered after implantation of a pedicle implant is the creation of a mobility chamber of the implant in the vertebral pedicle between the screw and the inner part of the pedicle. This mobility is due to a cell lysis resulting from the intense pressure on the cell at the time of the implantation, between the core of the screw and the cortical bone.

BRIEF SUMMARY OF THE INVENTION

The present invention aims to propose an implant device making it possible to resolve the various aforementioned drawbacks.

The implant device according to the invention, used to maintain a distraction or compression element that consists of a bar connected to implants through support means, or of a plate pierced with holes for the passage of the implants, and of the type comprising a threaded shank, as well as a head provided with a cavity for maneuvering thereof, and which has a spherical or partially spherical part intended to cooperate with a support piece able to pivot on said head and to be immobilized therein, said support piece including means for fastening and blocking a distraction or compression element, and it is essentially characterized in that said threaded part includes two zones, namely a distal end zone with a conical profile and the thread of which with wide turns is configured for cancellous bone, and a proximal zone with a conical profile with a taper angle smaller than that of said distal part, and the thread of which is fine and configured for the cortex of the bone, namely it includes fine and deep sharp threads, while the core is flat; and in that the two threads have the same pitch or very close pitches.

The configuration of the proximal part, i.e., its taper, even small, and its thread with a fine and deep spire associated with a flat core, makes it possible to avoid cell lysis and therefore to improve contact. The inner part of the pedicle is therefore less compressed, which causes better holding in the short, medium and long term.

The purpose of this thread is to have maximal intra-pedicle bone catching without excessive compression of the bone cell and to allow fast osteo-integration. This thread has the particularity of providing an intra-pedicle progression without lateral pressing stress responsible for pedicle fracture at the end of screwing. This thread is exclusively a pedicle thread.

According to one additional feature of the implant device according to the invention, it includes a cannula configured to allow the insertion of a pin provided with a density sensor.

According to another additional feature of the implant device according to the invention, the proximal zone has a taper of 1°, while the distal zone has a taper of 4°.

According to another additional feature of the implant device according to the invention, the thread of the proximal zone has a pitch smaller than that of the distal zone.

According to another additional feature of the implant device according to the invention, the difference in values of the pitches is less than 20%.

The distal zone includes a different thread with round fillets and the same depth as the thread of the proximal part. It has a sharp helix at its end. Its taper allows a gradual insertion without stress. It is provided with three slits parallel to the slope to perform a self-tapping function.

The sharp helix allows the implant to be inserted into the bone easily without having cortical micro-fractures responsible for a pedicle fracture onset, and it performs a self-perforation function.

It will be noted that a screw including such features is not able to be made easily. The thread is thus made in two steps: in a first one, the thread is made in the distal zone using a whirl cutter, then in a second one, the thread of the proximal zone is made by turning with an insert, with, between these two operations, a step for identifying the stopping point of the first operation and the starting point of the second operation.

BRIEF DESCRIPTION OF THE SEVERAL VIEWS OF THE DRAWINGS

The advantages and features of the implant device according to the invention will emerge more clearly from the following description relative to the appended drawings, which shows several non-limiting embodiments thereof.

DETAILED DESCRIPTION OF THE INVENTION

Figure 1:
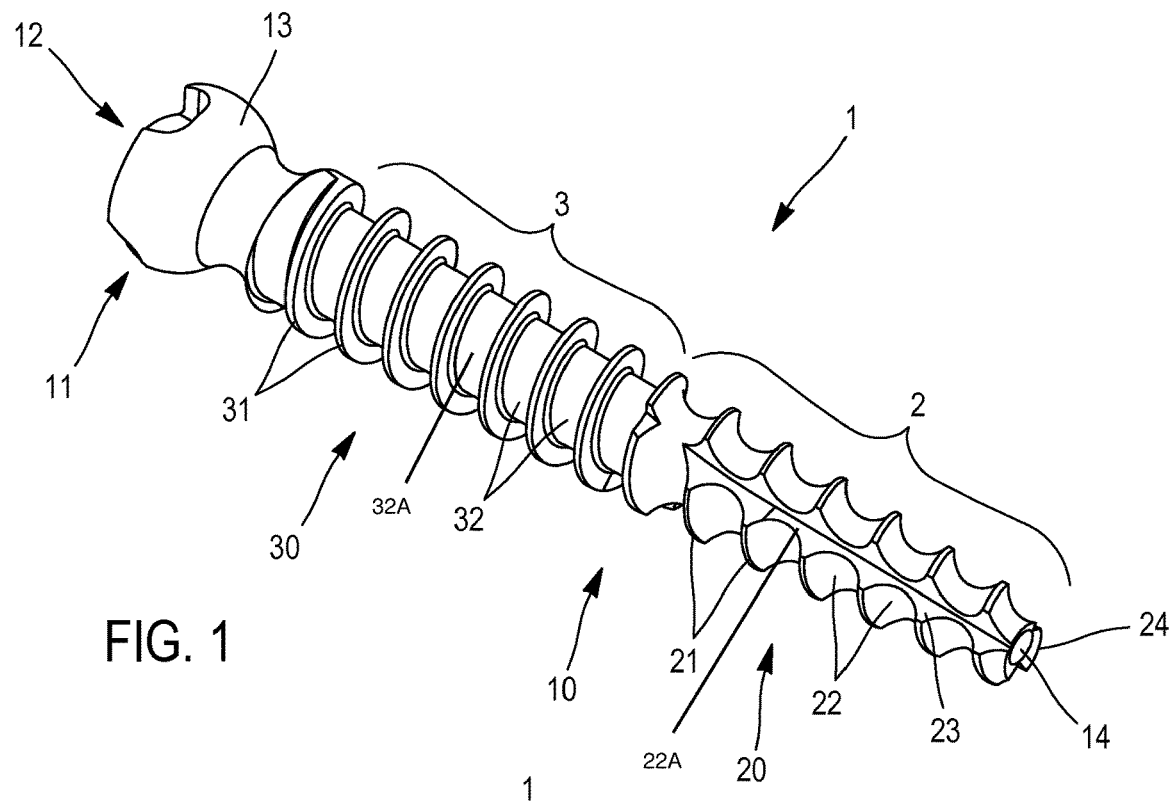
FIG. 1 shows a perspective view of an implant device according to the invention.
Figure 2:
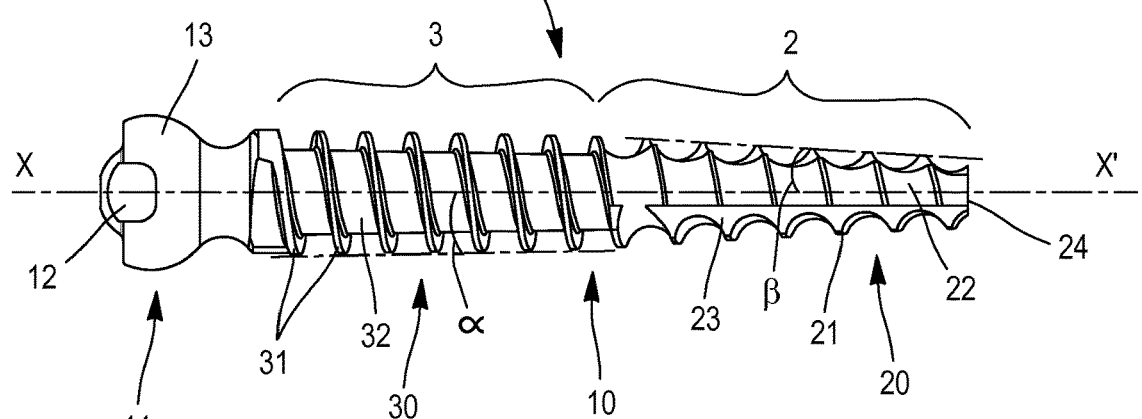
FIG. 2 shows a planar schematic view of the same implant device.

In reference to FIGS. 1 and 2, one can see an implant device according to the invention, comprising a threaded rod 1 intended to be associated with a support piece, not shown, designed to maintain a distraction or compression element consisting of a bar or the like according to document FR 2,880,254.

The threaded rod 1 includes a threaded part 10, a head 11 provided with a cavity 12 for maneuvering thereof, as well as a partially spherical part 13 allowing the pivoting cooperation of the support part, not shown.

According to the invention, one can see that the threaded part 10 includes two zones, namely a distal zone 2 and a proximal zone 3, extending between the distal zone 2 and the head 11.

The distal zone 2, which extends over ⅖ of the threaded part or threaded shank 10, has a distal conical profile with a distal taper angle relative to said longitudinal axis and a distal thread pitch; in the case at hand, preferably but non-limitingly, this distal taper angle β is 4° relative to the longitudinal axis XX'.

The proximal zone 3 has a proximal conical profile with a proximal taper angle relative to said longitudinal axis and a proximal thread pitch; in the case at hand, preferably but non-limitingly, it has the proximal taper angle α of 1° relative to the longitudinal axis XX'. The proximal taper angle is smaller than the distal taper angle.

The proximal zone is comprised of proximal core 32A and proximal threads 31 around the proximal core so as to define the proximal conical profile. The proximal core is comprised of proximal bottoms 32 between adjacent proximal threads 30. The thread 30 of the proximal zone 3 has, over ⅗ of the total length of the implant, fine and deep sharp turns 31 of 0.7 mm, while the proximal bottom 32 is flat. The purpose of this thread 30 is to have maximal intra-pedicle bone catching without excessive compression of the bone cell and to allow fast osteo-integration. This thread 30 has the particularity of providing an intra-pedicle progression without lateral pressing stress responsible for pedicle fracture at the end of screwing. This thread 30 is exclusively a pedicle thread.

The distal zone is comprised of a distal core 22A and distal threads 20 around the distal core so as to define said distal conical profile. The distal core is comprised of distal bottoms 22 being concave and between adjacent distal threads. The distal threads 20 can be round fillets 21, with the same depth as the thread 30 of the proximal part 3. The distal bottoms 22 are concave.

Preferably, the threads 20 and 30 have identical pitches. However, if the threads 20 and 30 of the zones, respectively distal 2 and proximal 3, are different, they then have very close values, and the pitch of the thread 30 is then smaller than that of the thread 30. In the case at hand, in the illustrated embodiment, the deviation between the two values is about 15%, which is less than 20%.

Figure 3:
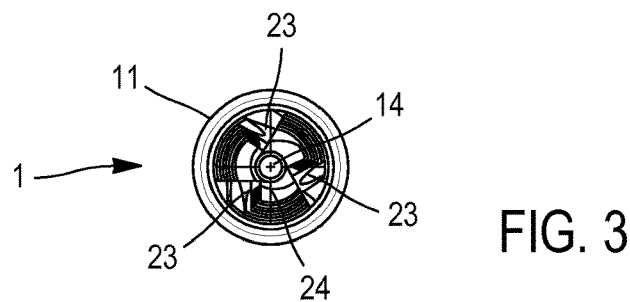
FIG. 3 shows a planar elevation view from one end of the same implant device.

The distal zone 2 also includes self-tapping notches or distal slits 23, of which there are three, as shown in FIG. 3.

The free end of the distal zone 2 is configured in a sharp helix or helix 24, which favors the insertion into the bone material.

In FIG. 3, one can also see that the implant 1 includes an axial cannula 14 through the threaded shank 10, which is intended for the insertion of a pin bearing a density sensor, making it possible to determine the location of the implant.

We claim:

1. An implant device, comprising:
a head being comprised of a partially spherical part with a cavity; and
a threaded shank and a longitudinal axis, comprising:
a proximal zone made integral with said head; and
a distal zone made integral with said proximal zone, said proximal zone being between said head and said distal zone,
wherein said proximal zone has proximal conical profile with a proximal taper angle relative to said longitudinal axis and a proximal thread pitch,
wherein said proximal zone is comprised of proximal core and proximal threads around said proximal core so as to define said proximal conical profile,
wherein said proximal core is comprised of proximal bottoms being flat and between adjacent proximal threads,
wherein said distal zone has a distal conical profile with a distal taper angle relative to said longitudinal axis and a distal thread pitch,
wherein said distal zone is comprised of a distal core and distal threads around said distal core so as to define said distal conical profile,
wherein said distal core is comprised of distal bottoms being concave and between adjacent distal threads, and
wherein said proximal taper angle is smaller than said distal taper angle.

2. The implant device, according to claim 1, wherein said threaded shank is further comprised of a cannula through said head and said threaded shank.

3. The implant device, according to claim 1, wherein said proximal taper angle is 1 degree, and wherein said distal taper angle is 4 degrees.

4. The implant device, according to claim 1, wherein said proximal thread pitch is smaller than said distal thread pitch.

5. The implant device, according to claim 4, wherein said proximal thread pitch is less than 20% smaller than said distal thread pitch.

6. The implant device, according to claim 1, wherein said distal threads 21 are comprised of round filets.

7. The implant device, according to claim 1, wherein said distal zone is further comprised of a distal slit.

8. The implant device, according to claim 1, further comprising: a helix made integral with said distal zone, said distal zone being between said helix and said proximal zone.

* * * * *